(12) United States Patent
Pavlov et al.

(10) Patent No.: US 8,535,504 B2
(45) Date of Patent: Sep. 17, 2013

(54) ANALYSIS OF AN AUXILIARY LEVELER ADDITIVE IN AN ACID COPPER PLATING BATH

(75) Inventors: Michael Pavlov, Fair Lawn, NJ (US); Eugene Shalyt, Washington Township, NJ (US); Peter Bratin, Flushing, NY (US); Isaak Tsimberg, Brooklyn, NY (US)

(73) Assignee: ECI Technology, Inc., Totowa, NJ (US)

( * ) Notice: Subject to any disclaimer, the term of this patent is extended or adjusted under 35 U.S.C. 154(b) by 256 days.

(21) Appl. No.: 13/065,939

(22) Filed: Apr. 2, 2011

(65) Prior Publication Data

US 2011/0266154 A1  Nov. 3, 2011

Related U.S. Application Data

(60) Provisional application No. 61/343,809, filed on May 3, 2010.

(51) Int. Cl.
*C25D 21/14* (2006.01)
*C05D 5/00* (2006.01)

(52) U.S. Cl.
USPC ............................... 205/81; 204/434; 205/787

(58) Field of Classification Search
USPC ................... 205/81, 775, 789.5, 794, 83, 787; 204/400, 416, 434
See application file for complete search history.

(56) References Cited

U.S. PATENT DOCUMENTS

| 7,205,153 B2 * | 4/2007 | Balisky ............................ 436/80 |
| 2003/0062266 A1 * | 4/2003 | Chalyt et al. .................... 205/81 |

OTHER PUBLICATIONS

Haak et al. "Cyclic Voltammetric Stripping Analysis of Acid Copper Sulfate Plating Baths," Plating and Surface Finishing Mar. 1982 60(3) pp. 62-66.*

* cited by examiner

*Primary Examiner* — Alex Noguerola
(74) *Attorney, Agent, or Firm* — D. Morgan Tench

(57) ABSTRACT

An auxiliary leveler additive that cannot be analyzed by conventional CVS methods for acid copper plating baths is analyzed by cyclic voltammetry at a platinum rotating disk electrode from its effect on the anodic current at very positive potentials.

15 Claims, 7 Drawing Sheets

ANALYSIS OF AN AUXILIARY LEVELER ADDITIVE IN AN ACID COPPER PLATING BATH

CROSS REFERENCE TO RELATED APPLICATIONS

This application claims priority to U.S. Provisional Application No. 61/343,809 filed May 3, 2010, which has the same inventors.

BACKGROUND OF THE INVENTION

1. Field of the Invention

This invention is concerned with analysis of organic additives and contaminants in plating baths as a means of providing control over the deposit properties.

2. Description of the Related Art

Electroplating baths typically contain organic additives whose concentrations must be closely controlled in the low parts per million range in order to attain the desired deposit properties and morphology. One of the key functions of such additives is to level the deposit by suppressing the electrodeposition rate at protruding areas in the substrate surface and/or by accelerating the electrodeposition rate in recessed areas. Accelerated deposition may result from mass-transport-limited depletion of a suppressor additive species that is rapidly consumed in the electrodeposition process, or from accumulation of an accelerating species that is consumed with low efficiency. The most sensitive methods available for detecting leveling additives in plating baths involve electrochemical measurement of the metal electrodeposition rate under controlled hydrodynamic conditions for which the additive concentration in the vicinity of the electrode surface is well-defined.

Cyclic voltammetric stripping (CVS) analysis [D. Tench and C. Ogden, J. Electrochem. Soc. 125, 194 (1978)] is the most widely used bath additive control method and involves cycling the potential of an inert electrode (e.g., Pt) in the plating bath between fixed potential limits so that metal is alternately plated on and stripped from the electrode surface. Such potential cycling is designed to establish a steady state for the electrode surface so that reproducible results are obtained. Accumulation of organic films or other contaminants on the electrode surface can be avoided by periodically cycling the potential of the electrode in the plating solution without organic additives and, if necessary, polishing the electrode using a fine abrasive. Cyclic pulse voltammetric stripping (CPVS), also called cyclic step voltammetric stripping (CSVS), is a variation of the CVS method that employs discrete changes in potential during the analysis to condition the electrode so as to improve the measurement precision [D. Tench and J. White, J. Electrochem. Soc. 132, 831 (1985)]. A rotating disk electrode configuration is typically employed for both CVS and CPVS analysis to provide controlled hydrodynamic conditions.

For CVS and CPVS analyses, the metal deposition rate may be determined from the current or charge passed during metal electrodeposition but it is usually advantageous to measure the charge associated with anodic stripping of the metal from the electrode. A typical CVS/CPVS rate parameter is the stripping peak area ($A_r$) for a predetermined electrode rotation rate. The CVS method was first applied to control copper pyrophosphate baths (U.S. Pat. No. 4,132,605 to Tench and Ogden) but has since been adapted for control of a variety of other plating systems, including the acid copper sulfate baths that are widely used by the electronics industry [e.g., R. Haak, C. Ogden and D. Tench, Plating Surf. Fin. 68(4), 52 (1981) and Plating Surf. Fin. 69(3), 62 (1982)].

Acid copper sulfate electroplating baths require a minimum of two types of organic additives to provide deposits with satisfactory properties and good leveling characteristics. The suppressor additive (also called the "polymer", "carrier", or "wetter", depending on the bath supplier) is typically a polymeric organic species, e.g., high molecular weight polyethylene or polypropylene glycol, which adsorbs strongly on the copper cathode surface to form a film that sharply increases the overpotential for copper deposition. This prevents uncontrolled copper plating that would result in powdery or nodular deposits. An anti-suppressor additive (also called the "brightener", "accelerator" or simply the "additive", depending on the bath supplier) is required to counter the suppressive effect of the suppressor and provide the accelerated deposition within substrate recesses needed for leveling. Plating bath vendors typically provide additive solutions that may contain leveling additives of more than one type, as well as other organic and inorganic addition agents. The suppressor additive may be comprised of more than one chemical species and generally involves a range of molecular weights.

Acid copper sulfate baths function well for plating the relatively large surface pads, through-holes and vias found on printed wiring boards (PWB's) and have been adapted for plating fine trenches and vias in dielectric material on semiconductor chips. The electronics industry transitioned from aluminum to copper as the basic metallization for semiconductor integrated circuits (IC's) in order to increase device switching speed and enhance electromigration resistance. The leading technology for fabricating copper IC chips is the "Damascene" process (see, e.g., P. C. Andricacos, Electrochem. Soc. Interface, Spring 1999, p. 32; U.S. Pat. No. 4,789,648 to Chow et al.; U.S. Pat. No. 5,209,817 to Ahmad et al.), which depends on copper electroplating to provide complete filling of the fine features involved. The organic additives in the bath must be closely controlled since they provide the copper deposition rate differential required for bottom-up filling.

As the feature size for the Damascene process shrank below 0.2 μm, it became desirable to utilize a third organic additive in the acid copper bath in order to avoid overplating the trenches and vias. Note that excess copper on Damascene plated wafers is typically removed by chemical mechanical polishing (CMP) but the copper layer must be uniform for the CMP process to be effective. The third additive is called the "leveler" (or "booster", depending on the bath supplier) and is typically an organic compound containing nitrogen or oxygen that also tends to decrease the copper plating rate. Leveler additive species tend to exert a relatively strong decelerating effect on the copper electrodeposition rate but are typically present in the plating bath at very low concentration so that their decelerating effect is weaker than that of suppressor additives. Due to their low concentration, leveler species tend to function under diffusion control.

In order to attain good bottom-up filling and avoid overplating of ultra-fine chip features in the Damascene process, the concentrations of all three additives must be accurately analyzed and controlled. The suppressor, anti-suppressor and leveler concentrations in acid copper sulfate baths can all be determined by CVS analysis methods based on the effects that these additives exert on the copper electrodeposition rate. At the additive concentrations typically employed, the effect of the suppressor in reducing the copper deposition rate is usually much stronger than that of the leveler so that the concentration of the suppressor can be determined by the usual CVS response curve or dilution titration analysis [W. O.

Freitag, C. Ogden, D. Tench and J. White, Plating Surf. Fin. 70(10), 55 (1983)]. Likewise, the anti-suppressor concentration can be determined by the linear approximation technique (LAT) or modified linear approximation technique (MLAT) described by R. Gluzman [Proc. 70th Am. Electroplaters Soc. Tech. Conf., Sur/Fin, Indianapolis, Ind. (June 1983)]. A method for measuring the leveler concentration in the presence of interference from both the suppressor and anti-suppressor is described in U.S. Pat. No. 6,572,753 to Chalyt et al.

Recently, an auxiliary leveler additive for acid copper baths has been developed for electrodepositing copper in through-silicon vias (TSV's) used for three-dimensional assembly of integrated circuits. Through-silicon vias interconnect stacked flip chips and are typically larger than Damascene vias. The auxiliary leveler additive has little or no effect on the copper electrodeposition rate in acid copper electroplating baths or supporting electrolytes thereof and cannot be analyzed by conventional CVS methods.

SUMMARY OF THE INVENTION

The present invention provides a method for determining the concentration of an auxiliary leveler additive in an acid copper electroplating bath that cannot be detected by conventional CVS methods. In the method of the invention, the auxiliary leveler additive is analyzed by cyclic voltammetry at a noble metal rotating disk electrode from its effect on the anodic current at very positive potentials (in the oxygen evolution region).

In a preferred embodiment, a predetermined baseline current is subtracted from the anodic currents used for the analysis so as to enhance sensitivity to the auxiliary leveler additive, which exerts little effect on smaller anodic currents. It is also preferable that the analysis be performed using the charge corresponding to integration of the anodic currents over a predetermined potential range (after subtraction of the baseline current). In a most preferred embodiment, the charges measured for calibration and measurement solutions are normalized with respect to the charge measured for a background electrolyte (not containing the auxiliary leveler additive).

The present invention further provides an apparatus for automated application of the method of the invention. The apparatus comprises a computing device that is interfaced with suitable electronic and mechanical equipment, and includes a memory element with a stored algorithm for performing at least the basic steps of the method. The computing device may comprise a computer with integrated components, or may comprise separate components, a microprocessor and a memory device that includes the memory element, for example. The memory element may be of any suitable type, including computer hard drive, microprocessor chip, read-only memory (ROM) chip, programmable read-only memory (PROM) chip, magnetic storage device, computer disk (CD) and digital video disk (DVD), for example.

The present invention is useful for improving the quality of deposits from acid copper plating baths by providing a method and an apparatus for measuring the concentrations of auxiliary leveler additives that cannot be detected by conventional CVS methods. The invention is particularly useful for controlling acid copper baths used to plate through-silicon vias (TSV's) used for three-dimensional assembly of integrated circuits. Other applications for which the invention could be used include Damascene plating and wafer level packaging, for example.

Further features and advantages of the invention will be apparent to those skilled in the art from the following detailed description, taken together with the accompanying drawings.

DETAILED DESCRIPTION OF THE INVENTION

Figure 1:
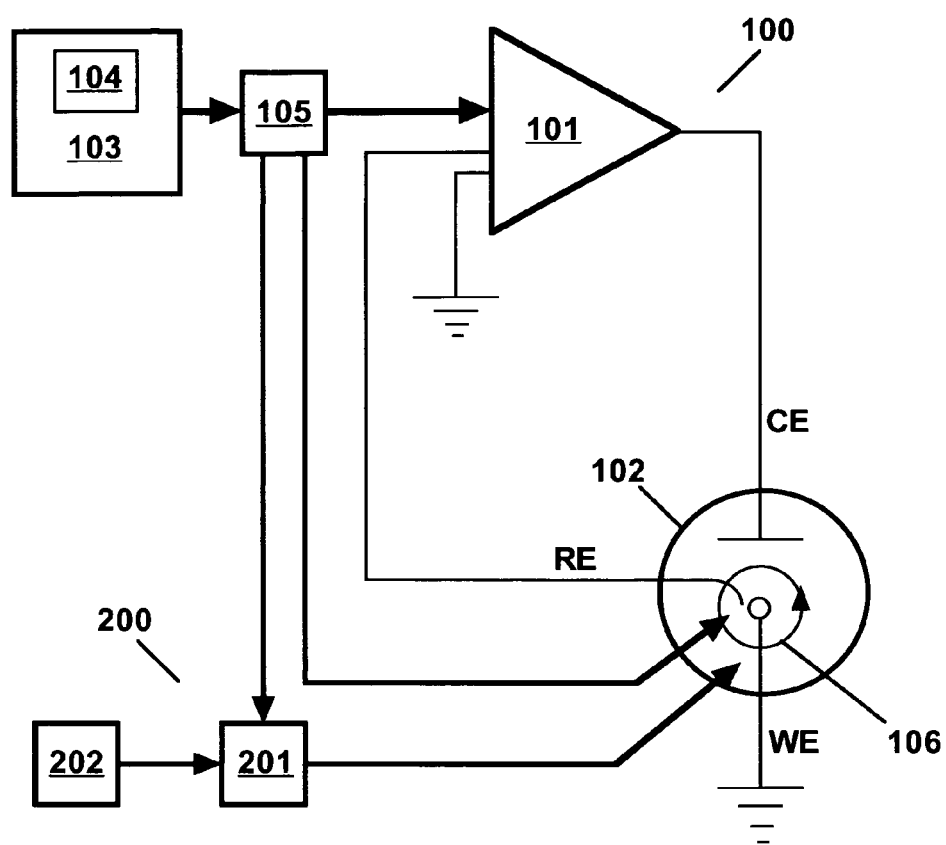
FIG. 1 is a schematic of an apparatus according to the invention.

Technical terms used in this document are generally known to those skilled in the art. The term "electrode potential", or simply "potential", refers to the voltage occurring across a single electrode-electrolyte interface. In practice, the electrode potential often includes an appreciable resistive voltage drop in the electrolyte, which typically remains constant and does not substantially affect voltammetric analysis results.

As used in this document, the terms "electroplating", "plating" and "electrodeposition" refer to copper electrodeposition and are equivalent. A "plating bath" is employed for practical copper plating and contains organic additives whose concentrations are controlled within ranges, whereas the corresponding "supporting electrolyte" typically has substantially the same inorganic composition as the plating bath but no organic additives. A "background electrolyte" comprises a supporting electrolyte containing one or more organic additives at predetermined concentrations. A preferred background electrolyte of the present invention comprises a suppressor additive, an anti-suppressor additive and a leveler additive at substantially the same concentrations as in the electroplating bath, or at a concentration for which the effect of the additive on the copper electrodeposition rate is saturated.

In this document, the term "standard addition" generally means addition of a predetermined quantity of a species (an additive, for example) to a predetermined volume of a solution (a background electrolyte or a measurement solution, for example). The predetermined quantity may be a predetermined weight of the species or a predetermined volume of a standard solution containing the species. The symbol "M" means molar concentration. The "volume fraction" is the volume of a plating bath solution added to a background electrolyte divided by the total volume of the resulting solution. Calibration data are typically handled as calibration curves or plots but such data may be tabulated and used directly, especially by a computer, and the terms "curve" or "plot" include tabulated data.

Voltammetric data may be generated by scanning the electrode potential at a constant rate or by stepping the potential, or by a combination of potential scanning and stepping. A "cyclic voltammogram" is a plot of current or current density (on the y-axis) versus the working electrode potential (on the x-axis) typically obtained by cycling the working electrode potential with time between fixed negative and positive limits. A "potentiostat" is an electronic device for controlling the potential of a working electrode by passing current between the working electrode and a counter electrode so as to drive the working electrode to a desired potential relative to a reference electrode. Use of a potentiostat avoids passing appreciable current through the reference electrode, which might change its potential. Operation in the three-electrode mode may also reduce errors in the electrode potential associated with the resistive voltage drop in the electrolyte.

The present invention provides a method and an apparatus for determining the concentration of an auxiliary leveler additive in an acid copper electroplating bath also containing a suppressor additive, an anti-suppressor additive and a leveler additive. The invention is suitable for analysis of acid copper plating baths comprising anions selected from the group consisting of sulfate, chloride, bromide, iodide, fluoroborate, sulfamate, alkylsulfonate, and mixtures thereof. The invention is especially suited to analysis of an auxiliary leveler additive in an acid copper sulfate electroplating bath.

In the method of the invention, an auxiliary leveler additive is analyzed by cyclic voltammetry at a noble metal rotating disk electrode (platinum, for example) from its effect on the anodic current at very positive potentials (in the oxygen evolution region). The potential of the electrode is typically cycled at a relatively fast scan rate (0.5 V/s, for example) over a relatively wide potential range (−0.275 V to +2.20 V vs. SSCE/M, for example), which provides reproducible results.

In a simple embodiment, the current in a relatively positive potential range (2.0 to 2.2 V vs. SSCE/M, for example) is used directly as a measure of the concentration of the auxiliary leveler additive, which tends to decrease the current in this potential range. It is preferable that a predetermined baseline current be subtracted from the anodic currents used for the analysis so as to enhance sensitivity to the auxiliary leveler additive, which exerts little effect on smaller anodic currents.

In a preferred embodiment, the analysis is performed using the charge corresponding to integration of the anodic current over a predetermined potential range (after subtraction of the baseline current). In a most preferred embodiment, the charges measured for calibration and measurement solutions are normalized with respect to the charge measured for a background electrolyte (not containing the auxiliary leveler additive).

A preferred method of the invention for determining the concentration of an auxiliary leveler additive in an acid copper electroplating bath also containing a suppressor additive, an anti-suppressor additive and a leveler additive, comprises the steps of: (1) cycling the potential of a rotating disk electrode between a predetermined negative potential limit and a predetermined positive potential limit in a background electrolyte of the acid copper electroplating bath comprising predetermined concentrations of sulfuric acid ($H_2SO_4$), copper ion ($Cu^{2+}$), chloride ion ($Cl^-$), the suppressor additive, the anti-suppressor additive and the leveler additive; (2) measuring the current response as the potential of the rotating disk electrode is cycled in step (1) so as to produce a normalization cyclic voltammogram; (3) selecting a baseline current ($I_{baseline}$) that is smaller than a maximum current ($I_{max}$) measured for the rotating disk electrode at the predetermined positive potential limit in step (2); (4) integrating the portion of the current in the normalization voltammogram that is greater than the baseline current so as to determine an $A_r(0)$ parameter; (5) cycling the potential of the rotating disk electrode between the predetermined negative potential limit and the predetermined positive potential limit in a plurality of calibration solutions comprising the background electrolyte and different predetermined concentrations of the auxiliary leveler additive; (6) measuring the current response as the potential of the rotating disk electrode is cycled in step (5) so as to produce a plurality of calibration cyclic voltammograms; (7) integrating the portion of the current in each of the calibration cyclic voltammograms that is greater than the baseline current so as to determine a plurality of $A_r$(calibration) parameters; (8) plotting the ratio $A_r$(calibration)/$Ar(0)$ as a function of the corresponding concentrations of the auxiliary leveler additive in the calibration solutions so as to generate a calibration curve; (9) cycling the potential of the rotating disk electrode between the predetermined negative potential limit and the predetermined positive potential limit in a measurement solution comprising predetermined volume fractions of the background electrolyte and a sample of the acid copper electroplating bath; (10) measuring the current response as the potential of the rotating disk electrode is cycled in step (9) so as to produce a measurement cyclic voltammogram; (11) integrating the portion of the current in the measurement cyclic voltammogram that is greater than the baseline current so as to determine an $A_r$(measurement) parameter; and (12) comparing the ratio $A_r$(measurement)/$A_r$(0) with the calibration curve to determine the concentration of the auxiliary leveler additive in the acid copper electroplating bath. The rotating disk electrode preferably comprises platinum but may comprise any noble metal including platinum, iridium, gold, osmium, palladium, rhenium, rhodium, ruthenium, and alloys thereof.

In a preferred embodiment, the rotating disk electrode is rotated at a relatively fast rate, preferably 2500 rpm or faster. The potential of the rotating disk electrode is preferably scanned at a constant rate in the range from 0.3 to 1.0 V/s between a negative potential limit in the range −0.325 to −0.125 vs. SSCE/M and a positive potential limit in the range 2.0 to 2.2 V vs. SSCE/M. Within the scope of the invention, the potential of the rotating disk electrode may be scanned at different rates within a cycle or in successive cycles, may be stepped within a cycle or in successive cycles, or a combination thereof. For voltammetric analyses, a plurality of potential cycles is typically employed to condition the working electrode surface so as to provide reproducible results. In this case, data are accepted only when a steady-state condition is reached, as indicated by substantially equivalent voltammograms or voltammetric features on successive cycles.

The invention may be used to analyze a variety of acid copper plating bath formulations, which typically comprise sulfuric acid ($H_2SO_4$), copper ion ($Cu^{2+}$), chloride ion ($Cl^-$), a suppressor additive, an anti-suppressor additive and a leveler additive. The composition of acid copper electroplating baths varies greatly depending on the type of bath and the supplier. High-acid baths typically contain 40-100 g/L copper sulfate, 140-240 g/L sulfuric acid and 25-100 ppm chloride ion. Low-acid baths typically contain 125-200 g/L copper sulfate, 1-40 g/L sulfuric acid and 25-100 ppm chloride ion. Acid copper plating bath additives are generally proprietary formulations supplied in the form of solutions that may contain more than one additive species or combination of additives. The chemical nature and concentrations of the additive species are typically not specified and may be changed from time to time by the supplier without notice.

Since chloride exerts a strong effect on the functioning of suppressor additives used in acid copper baths, its concentration should, if necessary, be adjusted to be within the target control range (typically, 25 to 100 ppm) in the plating bath sample being analyzed, and in the background electrolyte used for calibration. Variations in the chloride, sulfuric acid and copper ion concentrations within the ranges recommended by the bath supplier usually have a negligible effect on the analysis results.

Cyclic voltammetric measurements according to the invention are preferably made at a constant temperature (within ±0.5° C.) since errors resulting from temperature variations may be significant. Acid copper baths are typically operated at ambient temperature but measurements may be made at a higher or a lower temperature. The accuracy of the voltammetric measurements may be improved by employing a slightly elevated solution temperature (3° or 4° C. above room temperature, for example) that can be more consistently maintained. Analysis and calibration measurements should be performed at the same temperature.

The apparatus of the invention comprises: (1) an electrochemical analysis system that includes a potentiostat, an electrochemical cell, a working electrode comprising a noble metal, a counter electrode, and a reference electrode; (2) a computing device having a memory element with a stored algorithm operative to effect at least the basic steps of the method of the invention; and (3) an interface enabling the computing device to control the electrochemical analysis system so as to perform at least the basic steps of the method of the invention. Suitable electrochemical analysis systems, computing devices, memory elements, and interfaces for use in the apparatus of the invention are well-known to those skilled in the art. In a preferred embodiment, the electrochemical analysis system of the apparatus of the invention further includes a rotation motor for rotating the working electrode.

FIG. 1 shows a schematic representation of a preferred apparatus 100 of the invention. An electronic potentiostat 101 is preferably used to control the potential of a working electrode WE by passing current between working electrode WE and a counter electrode CE so as to drive working electrode WE to a desired potential relative to a reference electrode RE. These three electrodes are immersed in a plating solution contained in electrochemical cell 102. Use of potentiostat 101 avoids passing appreciable current through reference electrode RE, which might change its potential. However, the invention may be practiced using any other suitable device for controlling the potential of working electrode WE. The tip of reference electrode RE, or an extension thereof, is preferably located as close as practical to working electrode WE so as to minimize errors in the working electrode potential associated with solution resistance. Most commercial potentiostats include a current follower device (not shown) to avoid errors in the potential of working electrode WE associated with the resistance of the current measuring device.

Preferred apparatus 100 of FIG. 1 also comprises a computing device 103 having a memory element 104 with a stored algorithm for effecting at least the basic steps of the invention, and an interface 105 enabling computing device 103 to control the electrochemical analysis system. Memory element 104 may be any one or a combination of available memory elements, including a computer hard drive, a microprocessor chip, a read-only memory (ROM) chip, a programmable read-only memory (PROM) chip, a magnetic storage device, a computer disk (CD) and a digital video disk (DVD), for example. Memory element 104 may be an integral part of computing device 103 or may be a separate device. Interface 105 may be an integral part of computing device 103 or may be a separate device.

As depicted in FIG. 1, preferred apparatus 100 preferably also comprises a rotation motor 106 for rotating working electrode WE, which preferably has a rotating disk configuration. Rotation motor 106 is preferably controlled by computing device 103, either directly or via interface 105 (as shown). Separate interface devices may also be used for the electrochemical analysis system and the rotation motor.

In a preferred embodiment, the apparatus of the invention further comprises at least one dosing system 200 comprising a liquid metering device 201 connected to a reservoir 202 containing a liquid to be metered into cell 102. Metering device 201 may be of any suitable type, a metering pump or a syringe, for example. Metering device 201 is preferably also controlled by computer 103, either directly or via interface 105 (as shown). In a most preferred embodiment, the apparatus of the invention comprises three dosing systems: one for adding samples of the plating solution to cell 102 from a plating tank; one for adding background electrolyte to cell 102 from a first reservoir; and one for adding auxiliary leveler additive solution to cell 102 from a second reservoir. In this case, the analysis of the invention may be fully automated. Preferably, the apparatus of the invention further comprises a means of rinsing cell 102 with pure water between analyses to avoid significant cross-contamination.

The apparatus of the invention preferably further comprises a means of measuring and controlling the temperature of the solution in cell 102, an immersion heater in conjunction with a thermocouple or thermistor, for example, or a cell water jacket through which a liquid from a temperature controller is circulated, for example. Such means of controlling temperature are well-known in the art.

The inert working electrode for CVS measurements may comprise any suitable electrically conducting material that is stable in the plating solution under the conditions used for the voltammetric analysis but preferably comprises a noble metal, for example, platinum, iridium, gold, osmium, palladium, rhenium, rhodium, ruthenium, and alloys thereof. A preferred rotating disk electrode is comprised of a platinum metal disk (3-5 mm diameter), with an electrical contact wire on the backside, embedded flush with one end of an insulating plastic cylinder (10-20 mm diameter). The rotating disk electrode may be fabricated by press fitting the metal disk into a hole in the plastic but is preferably fabricated by hot pressing, which forms a seal between the metal and the plastic that prevents intrusion of the solution. A suitable plastic for mounting rotating disk electrodes by hot pressing is polytrifluorochloroethylene (Kel-F®). The rotating disk electrode is usually rotated at a constant rate (100-10,000 rpm) but the electrode rotation may be modulated with time.

An electronic potentiostat in conjunction with a counter electrode and a reference electrode is preferably employed to provide precise control of the working electrode potential. Any suitable reference electrode, silver-silver chloride (SSCE), mercury-mercury sulfate, or saturated calomel electrode (SCE), for example, may be employed. A double junction may be used to extend the life of the reference electrode by inhibiting intrusion of plating bath species. The counter electrode may be a reactive metal or an inert metal. Practically any electrical conductor that resists oxidation and reduction in the plating solution may be used as an inert counter electrode, including metals, alloys and conducting oxides. A preferred inert counter electrode material is 316 stainless steel, which is highly oxidation-resistant and relatively inexpensive, but other types of stainless steel or other oxidation-resistant alloys (Inconel, for example) may also be used. Other suitable inert counter electrode materials include noble metals, for example, platinum, iridium, gold, osmium, palladium, rhenium, rhodium, ruthenium, and alloys thereof.

Although less preferred, the invention may be practiced by using the current in a relatively positive potential range as a measure of the concentration of the auxiliary leveler additive. In this case, the method for determining the concentration of an auxiliary leveler additive in an acid copper electroplating bath also containing a suppressor additive and an anti-suppressor additive, comprises the steps of: (1) cycling the potential of a rotating disk electrode between a predetermined negative potential limit and a predetermined positive potential limit in a background electrolyte of the acid copper electroplating bath comprising predetermined concentrations of sulfuric acid ($H_2SO_4$), copper ion ($Cu^{2+}$), chloride ion ($Cl^-$), a suppressor additive, an anti-suppressor additive and a leveler additive; (2) measuring a normalization anodic current at a predetermined measurement potential as the potential of the rotating disk electrode is cycled in step (1); (3) selecting a baseline anodic current ($I_{baseline}$) that is smaller than the normalization anodic current measured for the rotating disk electrode at the measurement potential in step (2); (4) subtracting the baseline anodic current from the normalization anodic current so as to determine a normalization parameter ($I_0$); (5) cycling the potential of the rotating disk electrode between the predetermined negative potential limit and the predetermined positive potential limit in a plurality of calibration solutions comprising the background electrolyte and different predetermined concentrations of the auxiliary leveler additive; (6) measuring a calibration anodic current at the predetermined measurement potential for each of the calibration solutions as the potential of the rotating disk electrode is cycled in step (5); (7) subtracting the baseline anodic current from each of the calibration anodic currents so as to determine a plurality of $I_{calibration}$ parameters; (8) plotting the ratio $I_{calibration}/I_0$ as a function of the corresponding concentrations of the auxiliary leveler additive in the calibration solutions so as to generate a calibration curve; (9) cycling the potential of the rotating disk electrode between the predetermined negative potential limit and the predetermined positive potential limit in a measurement solution comprising predetermined volume fractions of the supporting electrolyte and a sample of the acid copper electroplating bath; (10) measuring a measurement anodic current at the predetermined measurement potential as the potential of the rotating disk electrode is cycled in step (9); (11) subtracting the baseline anodic current from the measurement anodic current so as to determine an $I_{measurement}$ parameter; and (12) comparing the ratio $I_{measurement}/I_0$ with the calibration curve to determine the concentration of the auxiliary leveler additive in the acid copper electroplating bath.

DESCRIPTION OF A PREFERRED EMBODIMENT

In a preferred procedure, a calibration curve is generated by measuring $A_r(0)$ for a background electrolyte of the plating bath, and measuring $A_r$(calibration) for each of a plurality of calibration solutions resulting from standard addition of the auxiliary leveler additive to the background electrolyte. The background electrolyte preferably has substantially the same inorganic composition as the copper plating bath being analyzed and contains suppressor, anti-suppressor and leveler additives at predetermined optimum concentrations. The preferred calibration curve is a plot of $A_r$(calibration)/$A_r(0)$ as a function of the auxiliary leveler additive concentration in the calibration solutions. For the auxiliary leveler additive analysis, $A_r$(measurement) is preferably measured for a measurement solution comprising a predetermined volume fraction of a plating bath sample added to the background electrolyte.

The efficacy of the present invention was demonstrated via analysis of a Semitool GEN III auxiliary leveler additive in an acid copper sulfate plating bath. This auxiliary leveler additive is designated the "polymer" additive by the supplier. The background electrolyte contained 57 g/L Cu, 50 g/L $H_2SO_4$ and 80 mg/L chloride ion, and was saturated with suppressor, anti-suppressor and leveler additives. Cyclic voltammetric measurements were made under potentiostatic control using a Qualilab QL-10® plating bath analyzer (ECI Technology, Inc.). The working electrode was a 4-mm diameter platinum rotating disk electrode embedded (by hot pressing) flush with one end of a Kel-F cylinder (13 mm diameter) and rotated at 2500 rpm. The platinum rotating disk electrode was cycled at 0.5 V/s between −0.275 V and +2.20 V vs. SSCE/M (silver-silver chloride electrode modified by replacing the solution in a standard SSCE electrode with a saturated AgCl solution also containing 0.1 M KCl and 10 volume % sulfuric acid). The counter electrode was a stainless steel rod (6 mm diameter). During CVS measurements, the solution temperature was controlled at 24±0.5° C.

Figure 2:
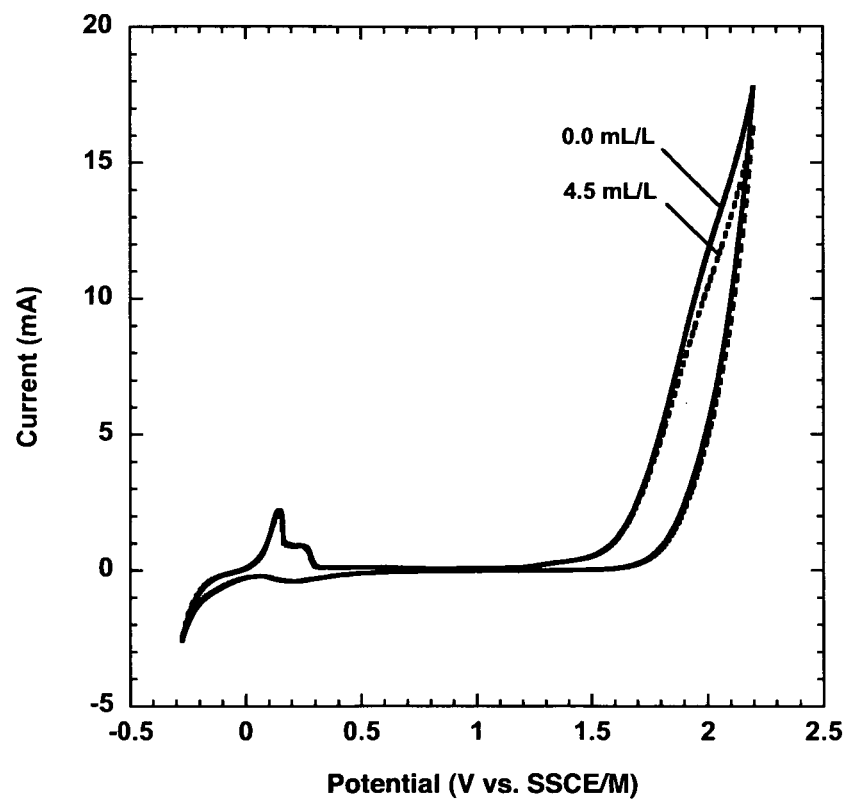
FIG. 2 shows cyclic voltammograms for a Pt rotating disk electrode (2500 rpm) cycled at 0.5 V/s between −0.275 and +2.20 V vs. SSCE/M in an acid copper background electrolyte with and without 4.5 mL/L of an auxiliary leveler additive.

FIG. 2 shows cyclic voltammograms for the Pt rotating disk electrode (2500 rpm) cycled at 0.5 V/s between −0.275 and +2.20 V vs. SSCE/M in the acid copper background electrolyte with and without 4.5 mL/L of the auxiliary leveler additive. The cathodic current negative of about 0.0 V corresponds to copper electrodeposition and the anodic peak between 0.0 and 0.3 V corresponds to stripping of the deposited copper from the Pt electrode. It is apparent that the auxiliary leveler additive has little effect on the copper electrodeposition and stripping currents, but has a significant effect on current for the anodic scan at potentials positive of about 1.9 V (oxygen evolution region). Note that the voltammogram for the background electrolyte without auxiliary leveler additive (0.0 mL/L) is the normalization cyclic voltammogram.

Figure 3:
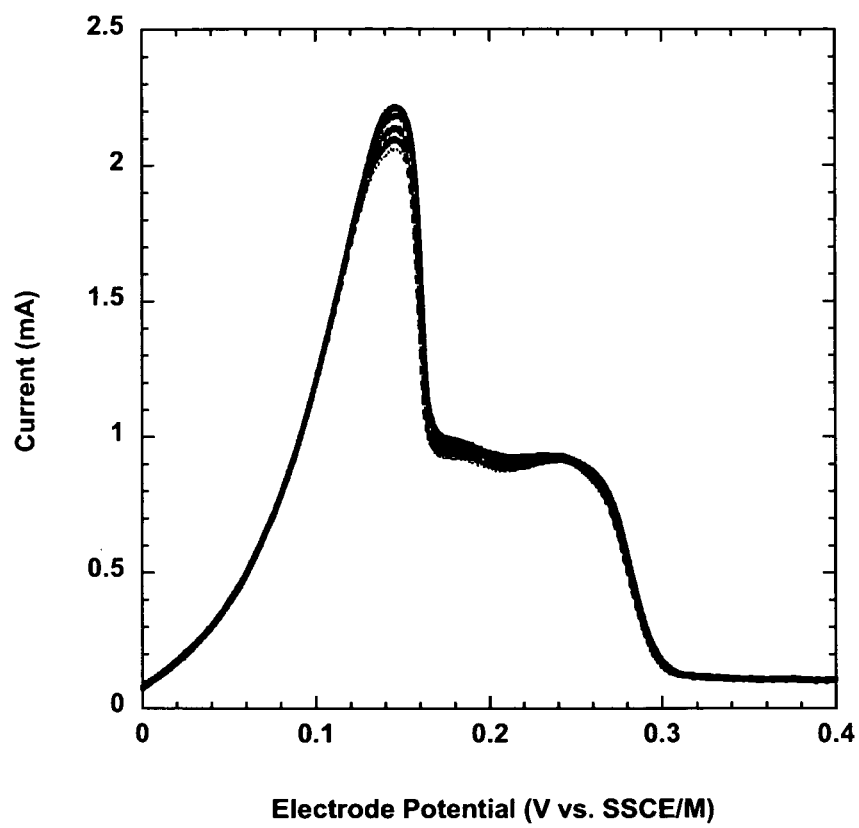
FIG. 3 shows the portions of the anodic scans of FIG. 2 between 0.0 and 0.4 V on an expanded current scale.

FIG. 3 shows the portions of the anodic scans of the voltammograms of FIG. 2 between 0.0 and 0.4 V on an expanded current scale. Cathodic potential scans and negative currents were omitted for ease of discussion. It is evident that the effect of the auxiliary leveler additive on the copper stripping peak area normally used for CVS analysis is small.

Figure 4:
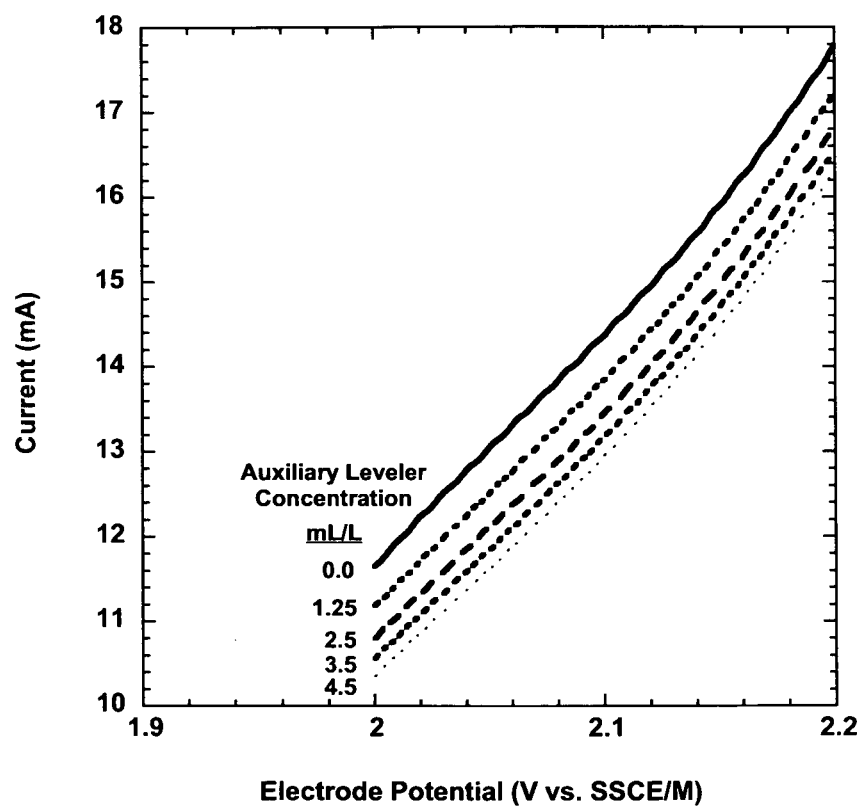
FIG. 4 shows the portions of the anodic scans of FIG. 2 between 2.0 and 2.2 V on an expanded current scale.

FIG. 4 shows the portions of the anodic scans of the voltammograms of FIG. 2 between 2.0 and 2.2 V on an expanded current scale. It is evident that the auxiliary leveler additive exerts a substantial effect on the current in this potential region, which decreases as the concentration of the auxiliary leveler additive is increased.

Figure 5:
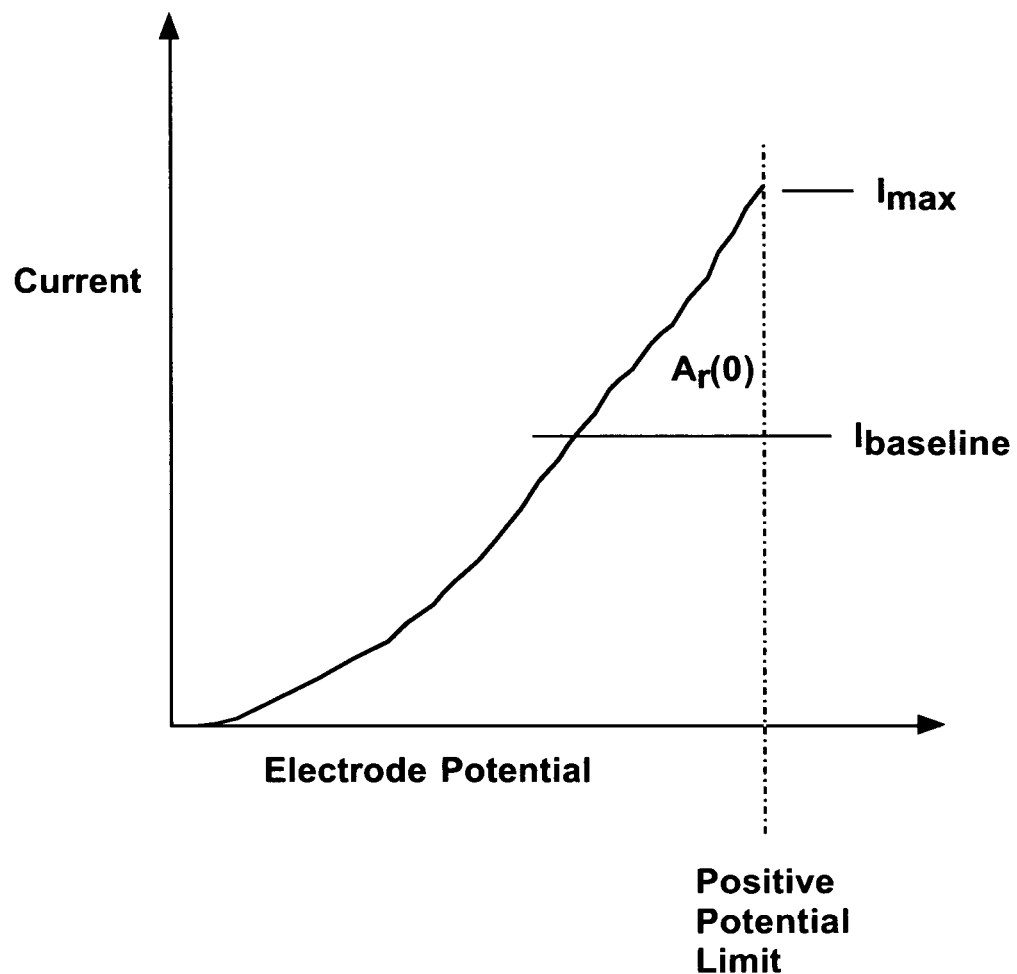
FIG. 5 is a schematic of the portion of the anodic scan for the background electrolyte of FIG. 4 illustrating the $I_{max}$, $I_{baseline}$ and $A_r(0)$ parameters of the invention.

FIG. 5 is a schematic of an anodic scan from 2.0 to 2.2V for a normalization cyclic voltammogram (background electrolyte with no auxiliary leveler additive) illustrating the $I_{max}$, $I_{baseline}$ and $A_r(0)$ parameters of the invention. The current at the positive potential limit defines the $I_{max}$ parameter. Note that $I_{max}$ is typically the highest positive current attained. The baseline current $I_{baseline}$ is preferably predetermined to be sufficiently smaller than $I_{max}$ to provide good sensitivity to the auxiliary leveler additive concentration. The value of $A_r(0)$ is determined by integrating the portion of the current that is greater than the baseline current, which corresponds to the area defined by the anodic scan of the normalization cyclic voltammogram, the baseline current ($I_{baseline}$), and the positive potential limit (as indicated in FIG. 5). Since the electrode potential is scanned so that the x-axis can be expressed in terms of time, $A_r(0)$ is typically expressed in units of charge (current×time).

Figure 6:
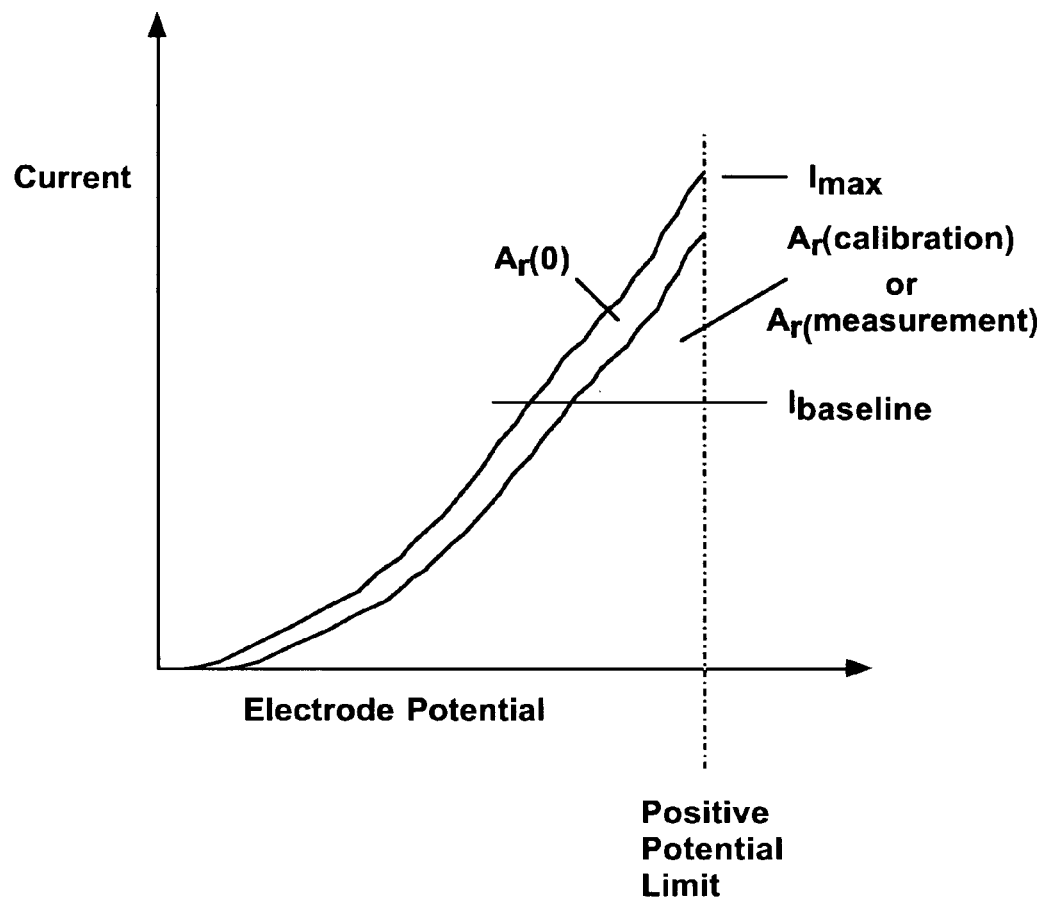
FIG. 6 is a schematic of the portions of the anodic scans for a background electrolyte and a calibration or measurement solution illustrating the relationship between the $A_r(0)$ and $A_r(calibration)$ or $A_r(measurement)$ parameters of the invention.

FIG. 6 is a schematic of the portions of the anodic scans for a background electrolyte (no auxiliary leveler additive) and a calibration or measurement solution (comprising auxiliary leveler additive) of FIG. 4 illustrating the relationship between the Ar(0) and $A_r$(calibration) or $A_r$(measurement) parameters of the invention. Note that $A_r(0)$ overlaps $A_r$(calibration) or $A_r$(measurement).

Figure 7:
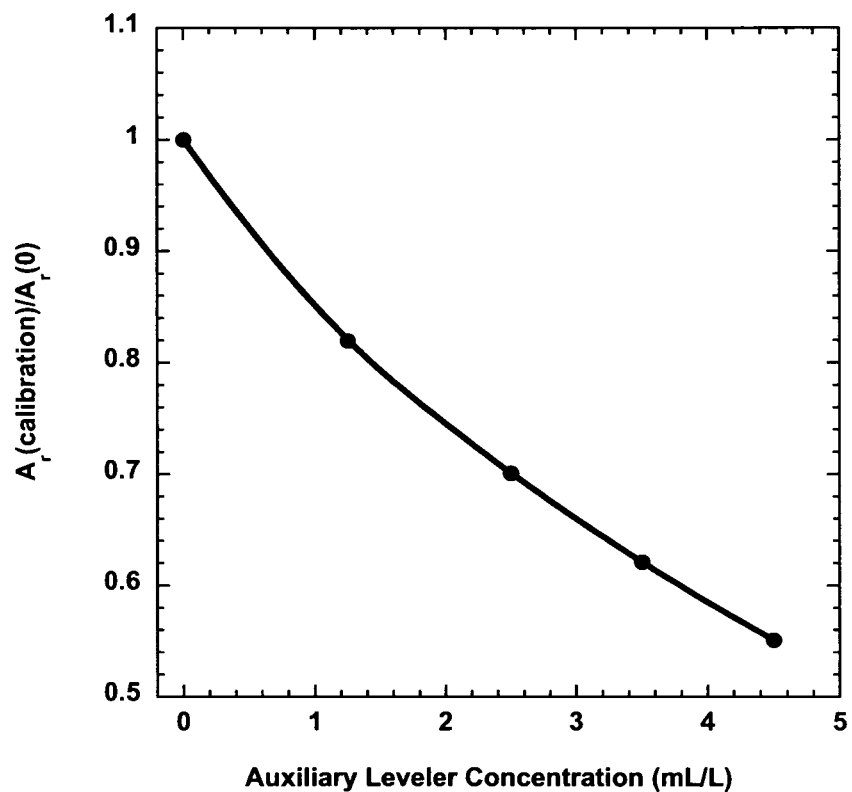
FIG. 7 depicts a calibration curve of $A_r(calibration)/A_r(0)$ vs. concentration of an auxiliary leveler additive in an acid copper electroplating bath according to the invention.

FIG. 7 depicts a calibration curve of $A_r$(calibration)/$A_r(0)$ vs. concentration of the auxiliary leveler additive in the acid copper background electrolyte. The $A_r$(calibration)/$A_r(0)$ parameter decreases monotonically with increasing concentration of the auxiliary leveler additive. Preferably, $A_r$(measurement)/$A_r(0)$ parameters are compared with the calibration curve by interpolation between data points to determine the concentration of the auxiliary leveler additive in the acid copper electroplating bath.

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for determining the concentration of an auxiliary leveler additive in an acid copper electroplating bath also containing a suppressor additive, an anti-suppressor additive and a leveler additive, comprising the steps of:
   (1) cycling the potential of a rotating disk electrode between a predetermined negative potential limit and a predetermined positive potential limit in the oxygen evolution region positive of 1.9 V vs. SSCE/M in a background electrolyte of the acid copper electroplating bath comprising predetermined concentrations of sulfuric acid ($H_2SO_4$), copper ion ($Cu^{2+}$), chloride ion ($Cl^-$), the suppressor additive, the anti-suppressor additive and the leveler additive;
   (2) measuring the current response as the potential of the rotating disk electrode is cycled in step (1) so as to produce a normalization cyclic voltammogram;
   (3) selecting a baseline current a ($I_{baseline}$) that is smaller than a maximum current ($I_{max}$) measured for the rotating disk electrode at the predetermined positive potential limit in step (2);
   (4) integrating the portion of the current in the normalization voltammogram that is greater than the baseline current so as to determine an $A_r(0)$ parameter;
   (5) cycling the potential of the rotating disk electrode between the predetermined negative potential limit and the predetermined positive potential limit in a plurality of calibration solutions comprising the background electrolyte and different predetermined concentrations of the auxiliary leveler additive;
   (6) measuring the current response as the potential of the rotating disk electrode is cycled in step (5) so as to produce a plurality of calibration cyclic voltammograms;
   (7) integrating the portion of the current in each of the calibration cyclic voltammograms that is greater than the baseline current so as to determine a plurality of $A_r$(calibration) parameters;
   (8) plotting the ratio $A_r$(calibration)/Ar(0) as a function of the corresponding concentrations of the auxiliary leveler additive in the calibration solutions so as to generate a calibration curve;
   (9) cycling the potential of the rotating disk electrode between the predetermined negative potential limit and the predetermined positive potential limit in a measurement solution comprising predetermined volume fractions of the supporting electrolyte and a sample of the acid copper electroplating bath;
   (10) measuring the current response as the potential of the rotating disk electrode is cycled in step (9) so as to produce a measurement cyclic voltammogram;
   (11) integrating the portion of the current in the measurement cyclic voltammogram that is greater than the baseline current so as to determine an $A_r$(measurement) parameter; and
   (12) comparing the ratio $A_r$(measurement)/$A_r(0)$ with the calibration curve to determine the concentration of the auxiliary leveler additive in the acid copper electroplating bath.

2. The method of claim 1, wherein the rotating disk electrode comprises a noble metal selected from the group consisting of platinum, iridium, gold, osmium, palladium, rhenium, rhodium, ruthenium, and alloys thereof.

3. The method of claim 1, wherein the rotation rate of the rotating disk electrode is 2500 rpm or greater.

4. The method of claim 1, wherein the potential of the rotating disk electrode is scanned at a constant rate in the range from 0.3 to 1.0 V/s.

5. The method of claim 1, wherein the potential of the rotating disk electrode is scanned between a negative potential limit in the range −0.325 to −0.125 vs. SSCE/M and a positive potential limit in the range 2.0 to 2.2 V vs. SSCE/M.

6. The method of claim 1, wherein the acid copper electroplating bath comprises 40-200 g/L copper sulfate, 1-240 g/L sulfuric acid and 25-100 ppm chloride ion.

7. A method for determining the concentration of an auxiliary leveler additive in an acid copper electroplating bath also containing a suppressor additive, an anti-suppressor additive and a leveler additive, comprising the steps of:
   (1) cycling the potential of a rotating disk electrode between a predetermined negative potential limit and a predetermined positive potential limit in a background electrolyte of the acid copper electroplating bath comprising predetermined concentrations of sulfuric acid ($H_2SO_4$), copper ion ($Cu^{2+}$), chloride ion ($Cl^-$), the suppressor additive, the anti-suppressor additive and the leveler additive;
   (2) measuring a normalization anodic current at a predetermined measurement potential as the potential of the rotating disk electrode is cycled in step (1);
   (3) selecting a baseline anodic current ($I_{baseline}$) that is smaller than the normalization anodic current measured for the rotating disk electrode at the measurement potential in step (2);
   (4) subtracting the baseline anodic current from the normalization anodic current so as to determine a normalization parameter ($I_0$);
   (5) cycling the potential of the rotating disk electrode between the predetermined negative potential limit and the predetermined positive potential limit in a plurality of calibration solutions comprising the background electrolyte and different predetermined concentrations of the auxiliary leveler additive;

(6) measuring a calibration anodic current at the predetermined measurement potential for each of the calibration solutions as the potential of the rotating disk electrode is cycled in step (5);

(7) subtracting the baseline anodic current from each of the calibration anodic currents so as to determine a plurality of $I_{calibration}$ parameters;

(8) plotting the ratio $I_{calibration}/I_0$ as a function of the corresponding concentrations of the auxiliary leveler additive in the calibration solutions so as to generate a calibration curve;

(9) cycling the potential of the rotating disk electrode between the predetermined negative potential limit and the predetermined positive potential limit in a measurement solution comprising predetermined volume fractions of the supporting electrolyte and a sample of the acid copper electroplating bath;

(10) measuring a measurement anodic current at the predetermined measurement potential as the potential of the rotating disk electrode is cycled in step (9);

(11) subtracting the baseline anodic current from the measurement anodic current so as to determine an $I_{measurement}$ parameter; and

(12) comparing the ratio $I_{measurement}/I_0$ with the calibration curve to determine the concentration of the auxiliary leveler additive in the acid copper electroplating bath.

8. The method of claim 7, wherein the rotating disk electrode comprises a noble metal selected from the group consisting of platinum, iridium, gold, osmium, palladium, rhenium, rhodium, ruthenium, and alloys thereof.

9. The method of claim 7, wherein the rotation rate of the rotating disk electrode is 2500 rpm or greater.

10. The method of claim 7, wherein the potential of the rotating disk electrode is scanned at a constant rate in the range from 0.3 to 1.0 V/s.

11. The method of claim 7, wherein the potential of the rotating disk electrode is scanned between a negative potential limit in the range −0.325 to −0.125 vs. SSCE/M and a positive potential limit in the range 2.0 to 2.2 V vs. SSCE/M.

12. The method of claim 7, wherein the acid copper electroplating bath comprises 40-200 g/L copper sulfate, 1-240 g/L sulfuric acid and 25-100 ppm chloride ion.

13. An apparatus for determining the concentration of an auxiliary leveler additive in an acid copper electroplating bath also containing a suppressor additive and an anti-suppressor additive, comprising:
an electrochemical analysis system, comprising
a potentiostat,
an electrochemical cell,
a working electrode comprising a noble metal,
a counter electrode, and
a reference electrode;
a computing device having a memory element with a stored algorithm configured to perform at least the steps of the method of claim 1 or claim 7; and
an interface enabling the computing device to control the electrochemical analysis system configured so as to perform at least the steps of the method that the algorithm is configured to perform.

14. The apparatus of claim 13, further comprising:
a rotation motor for rotating the working electrode.

15. The apparatus of claim 13, further comprising:
at least one dosing system, comprising
a reservoir containing a liquid, and
a liquid metering device connected to the reservoir.

* * * * *